(12) United States Patent
Kuppuswamy et al.

(10) Patent No.: US 7,632,864 B2
(45) Date of Patent: Dec. 15, 2009

(54) GABAPENTIN ANALOGUES AND PROCESS THEREOF

(75) Inventors: Nagarajan Kuppuswamy, Bangalore (IN); Sivaramakrishnan Hariharan, Bangalore (IN); Venkatachalam Sankar Iyer, Bangalore (IN); Suresh Babu Balakrishnan, Bangalore (IN); Gopalakrishnan Krishnamurthi, Bangalore (IN); Ananda Kuppanna, Bangalore (IN); Muruga Poopati Raja Karuppiah, Bangalore (IN); Balaram Padmanabhan, Bangalore (IN); Aravinda Subrayashastry, Bangalore (IN); Gouriamma Vasudev Prema, Bangalore (IN); Shamala Narayanaswamy, Bangalore (IN)

(73) Assignees: Hikal Ltd., Bangalore (IN); Indian Institute Of Science, Bangalore (IN)

( * ) Notice: Subject to any disclaimer, the term of this patent is extended or adjusted under 35 U.S.C. 154(b) by 0 days.

(21) Appl. No.: 11/583,953

(22) Filed: Oct. 20, 2006

(65) Prior Publication Data

US 2007/0123591 A1   May 31, 2007

Related U.S. Application Data

(63) Continuation-in-part of application No. 11/079,481, filed on Mar. 15, 2005, now abandoned.

(51) Int. Cl.
  *A61K 31/195* (2006.01)
  *C07C 229/00* (2006.01)
(52) U.S. Cl. ..................... 514/561; 562/507
(58) Field of Classification Search ...................... None
  See application file for complete search history.

(56) References Cited

U.S. PATENT DOCUMENTS 6,103,932 A    8/2000   Horwell et al.

FOREIGN PATENT DOCUMENTS

WO   WO 99/14184   3/1999
WO   WO 02/00347   1/2002

*Primary Examiner*—Paul A Zucker

(57) ABSTRACT

The present invention relates to compounds trans (E) and cis (Z) stereoisomers of 4-t-butyl gabapentin of formula (11) and (12) and a process for the preparation of the said stereoisomers.

15 Claims, 13 Drawing Sheets

SCHEME I
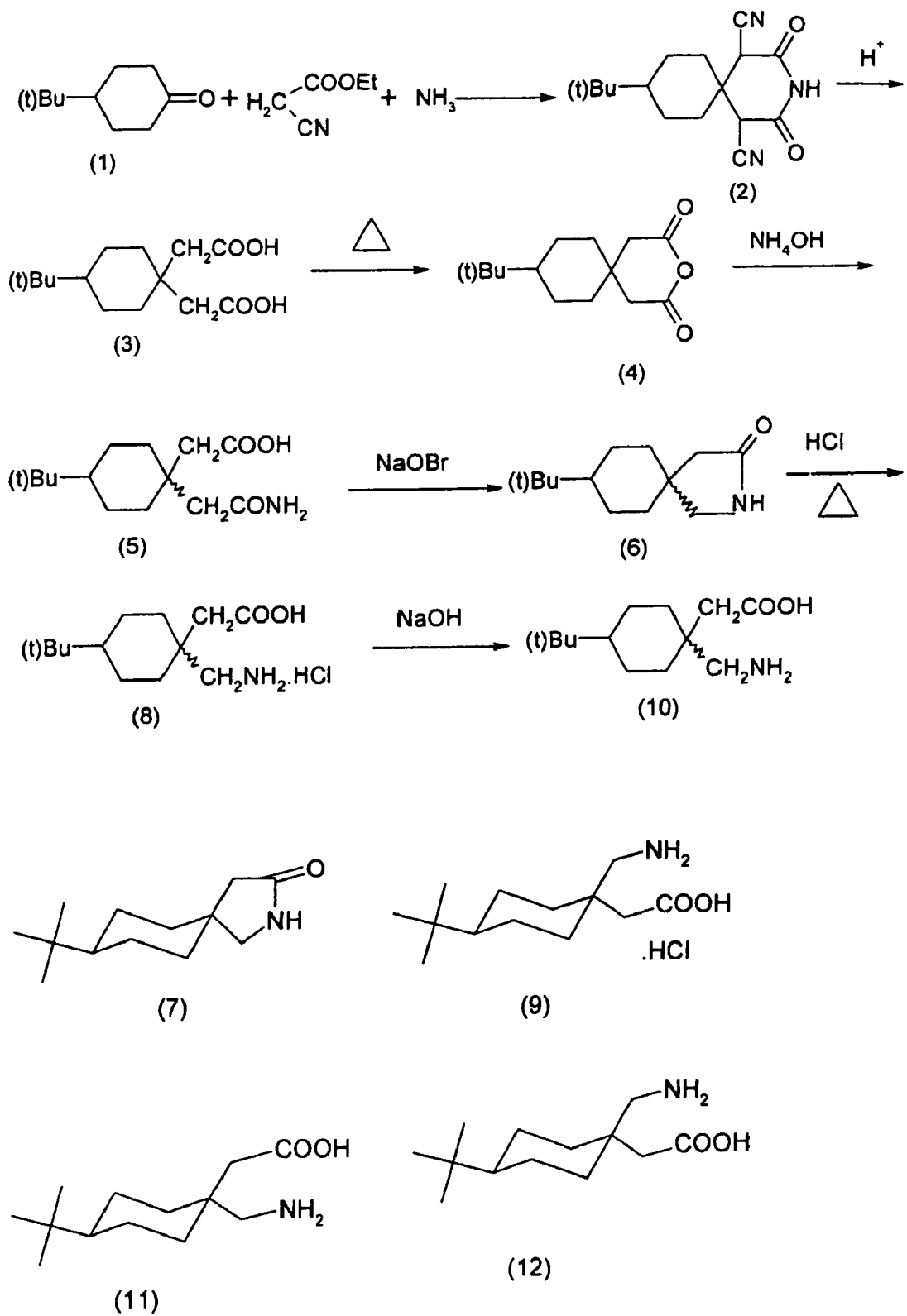

Table 1
Properties of t-butylgabapentin isomers
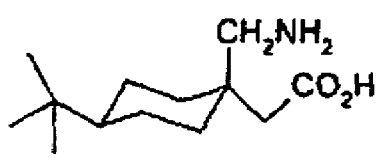
Z - Isomer (12)
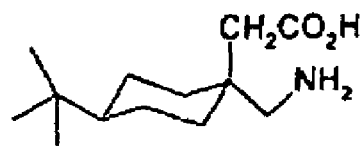
E - Isomer (11)
|  | Z - Isomer | E - Isomer |
|---|---|---|
| Base | | |
| MP | 183-184 | 182-183 |
| Proton NMR in | | |
| CD3OD | 2.34 (COCH2), 3.01 (NCH2), | 2.59 (COCH2), 2.87(NCH2), |
|  | 0.90(t-Bu) | 0.90(t-Bu) |
|  | | |
| M+ | 227 | 227 |
|  | | |
| HPLC RT | 12.064 | 12.245 |
|  | | |
| IR cm-1 | 1644, 1589, 1604, 1418 | 1650, 1526, 1494, 1403, |
|  | 1394, 1364, 1333,1309 | 1386,1297, 1168,1085, |
|  | 1250, 1172, 1134, 1109 | 1,022,980,944,915, |
|  | 1039, 984, 880, 854, | 896,875,790,762 |
|  | 761, 709, 629, 578 | 725,611,592 |
|  | | |
| HCl salt | | |
| mp | 188-189 | 189-190 |
| NMR in CD3 OD | 2.36 (COCH2), 3.06 (N-CH2), | 2.55 (COCH2), 2.97 (NCH2) |
|  | 0.91 (t-Bu) | 0.915 (t-Bu) |

Table 2

| Full refinement details | 4-t-butylgabapentin Z isomer (12) | 4-t-butylgabapentin E isomer (11) |
|---|---|---|
| Chemical formula | $C_{13}H_{25}N_1O_2$ | $C_{13}H_{25}N_1O_2$ |
| Formula weight | 227.3 | 227.3 |
| Crystal shape and color | Thin, Diamond shaped, colorless | Needles, colorless |
| Crystal size (mm) | 0.47×0.32×0.07 | 0.40×0.248×0.126 |
| Recrystallization solvent | $CH_3OH$ | $CH_3OH$ |
| Crystal system | Monoclinic | Orthorhombic |
| Space group | $P2_1/c$ | $Pca2_1$ |
| Unit cell dimensions | | |
| a (Å) | 19.790(6) | 6.598 (3) |
| b (Å) | 6.029(17) | 38.81 (2) |
| c (Å) | 11.171(3) | 10.623 (6) |
| α (deg) | 90 | 90 |
| β (deg) | 96.978 (5) | 90 |
| γ (deg) | 90 | 90 |
| Volume (Å$^3$) | 1321.8 (6) | 2720.0 (2) |
| Temperature | 293 K | 293 K |
| No. of formula units in unit cell (Z) | 4 | 8 |
| Linear absorption coefficient (μ) | 0.076 | 0.073 |
| Measured reflections | 9631 | 15018 |
| Independent reflections | 2709 | 3870 |
| Observed reflections [$|F|>4\sigma(F)$] | 1973 | 3502 |
| $R_{int}$ | 0.0377 | 0.0475 |
| θ range (°) | 1.04 - 27.14 | 1.57 - 23.25 |
| hkl range | h = -24 to 24; k = -7 to 7; l = -13 to 13 | h = -7 to 7; k = -41 to 43; l = -11 to 11 |
| Final R(%) for observed data | 5.69 | 7.52 |
| Final wR2(%) for observed data | 12.93 | 14.90 |
| Type of monochromator | Graphite | Graphite |
| Radiation | Mo Kα (λ = 0.71073 Å) | Mo Kα (λ = 0.71073 Å) |
| Density (g/cm$^3$)(calculated) | 1.142 | 1.110 |
| Method of structure solution | Direct methods | Direct methods |
| Method of refinement | Full matrix least square refinement on $F^2$ | Full matrix least square refinement on $F^2$ |
| H atom treatment | Located from difference Fourier map, isotropic refinement | Geometrically fixed in idealized positions, 'riding model' refinement |
| Weighting scheme | $w=1/[\sigma^2 x(Fo^2)+(0.0847xP)^2+]$ where, P = (max ($Fo^2$, 0) + 2$Fc^2$)/3 | $w=1/[\sigma^2 x(Fo^2)+(0.0305xP)^2+4.1036P]$ where, P = (max ($Fo^2$, 0) + 2$Fc^2$)/3 |
| Restraints / parameters | 0 / 245 | 3 / 413 |

| Full refinement details | 4-t-butylgabapentin Z isomer (12) | 4-t-butylgabapentin E isomer (11) |
|---|---|---|
| Definition of R, wR | $R1 = \Sigma \| \|F_o\| - \|F_c\| \| / \Sigma \|F_o\|$ <br> $wR2 = \{\Sigma[w(F_o^2 - F_c^2)^2] / \Sigma[w(F_o^2)^2]\}^{1/2}$ | $R1 = \Sigma \| \|F_o\| - \|F_c\| \| / \Sigma \|F_o\|$ <br> $wR2 = \{\Sigma[w(F_o^2 - F_c^2)^2] / \Sigma[w(F_o^2)^2]\}^{1/2}$ |
| Goodness - of - fit (S) | 1.088 | 1.113 |
| Residual electron density max / min. ($eÅ^{-3}$) | 0.27 / -0.23 | 0.22 / -0.19 |
| Average and max. Shift/esd | 0.003 / 0.013 | 0.04 / 0.65 |
| F (000) | 504 | 1008 |
| Absorption correction method | None | None |
| Type of Diffractometer | Bruker AXS SMART APEX CCD diffractometer | Bruker AXS SMART APEX CCD diffractometer |
| Diffraction geometry | Three circle | Three circle |
| Programs used | SMART[1], SAINT[1], SHELXS[2], SHELXL[3] | SMART[1], SAINT[1], SHELXS[2], SHELXL[3] |
| Flack parameter | - | 10 |

References:
1. Bruker, SMART, SAINT, XPREP AND SHELXTL. Bruker AXS Inc., 5465 East Cheryl Parkway, Madison, WI 53711-5373 USA (1998).
2. Sheldrick, G. M. SHELXS-97, A program for automatic solution of crystal structures, University of Göttingen, Göttingen (1997).
3. Sheldrick, G. M. SHELXL-97, A program for crystal structure refinement, University of Göttingen, Göttingen (1997).

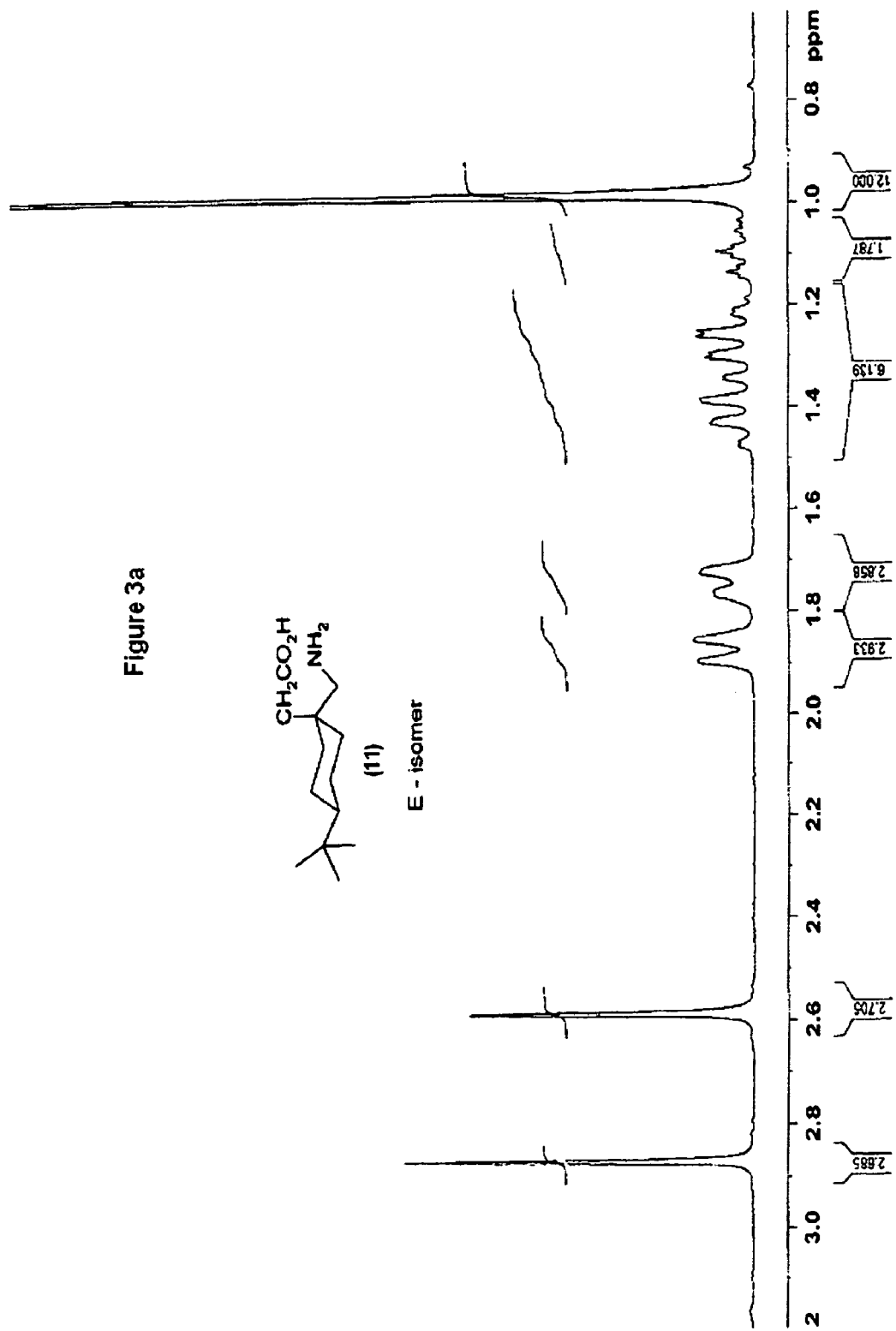

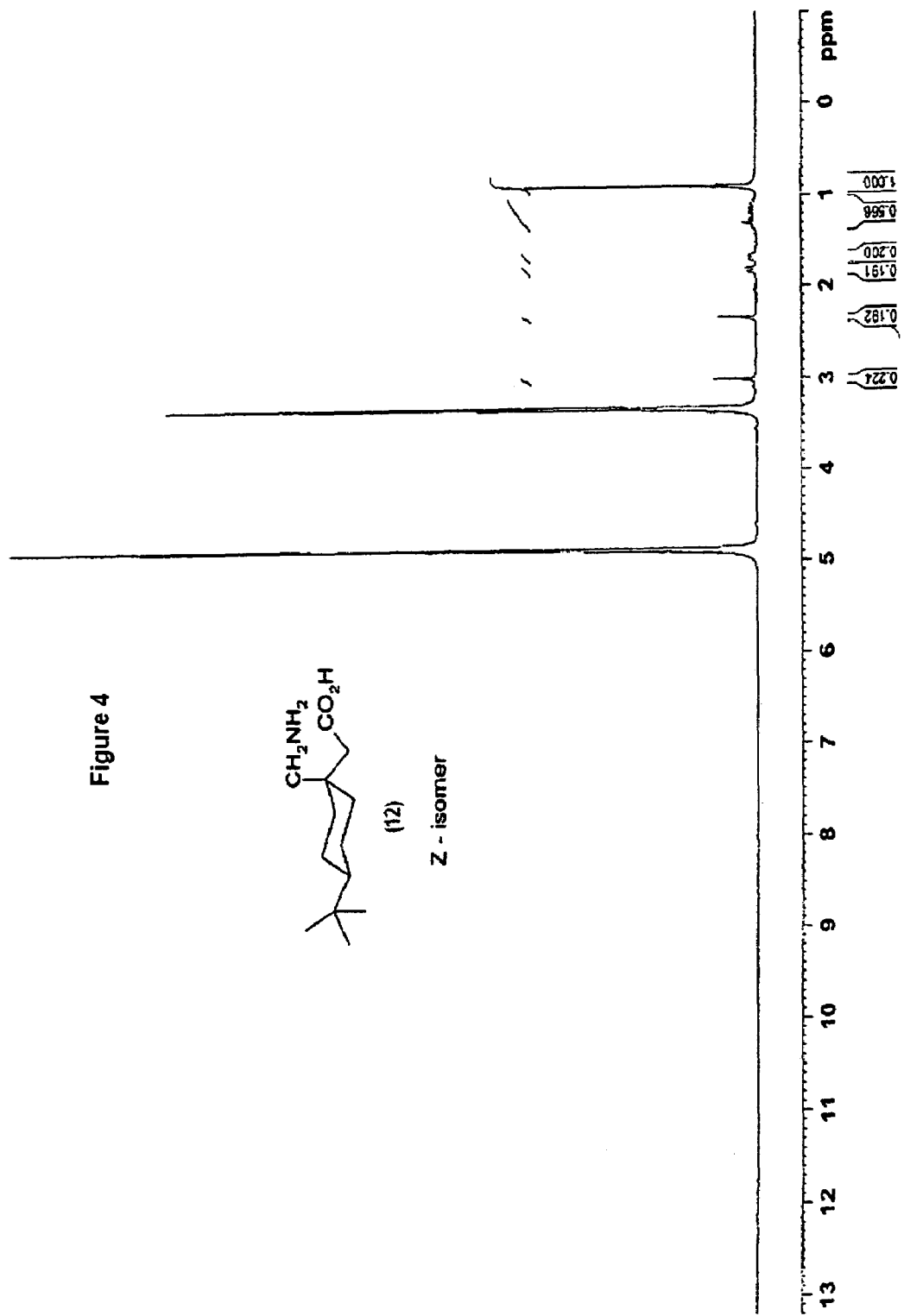

ORTEP diagrams of isomers of 4-t-butylgabapentin

4-t-butylgabapentin
E isomer (11)

4-t-butylgabapentin
Z isomer (12)

GABAPENTIN ANALOGUES AND PROCESS THEREOF

CROSS-REFERENCE TO RELATED PATENT APPLICATIONS

This application is a continuation-in-part of U.S. application Ser. No. 11/079,481, filed on Mar. 15, 2005 (now abandoned), of which the entire contents, including specification, figures and responses are incorporated by reference.

BACKGROUND OF THE INVENTION

1. Technical Field

The present invention relates to stereo isomers (E) and (Z) of 4-t-butyl gabapentin and a process for the preparation of the said stereoisomers.

2. Background and Prior Art Reference

Gabapentin, (1-aminomethyl)cyclohexane-1-acetic acid is an antiepileptic drug, which has been found to have pain-relieving properties. Additionally, it is claimed to have anti-anxiety activity as also beneficial properties in treating neurodegenerative diseases like Alzheimer's. Gabapentin and its analogues are reported to exert their activity by binding to the alpha 2-delta sub unit of calcium channel.

WO 99114184 reports the synthesis of gabapentin analogues 3-methyl, 4-methyl and 3,5-dimethyl gabapentin and their biological activity. In all these analogues the aminomethyl group could preferentially occupy the equatorial position in the more stable conformation along with certain percentage in the axial position. However the exact conformation in which these bind to a receptor is not known. If the energy differences are not significant, binding with the aminomethyl group in the axial position cannot be ruled out. This document does not claim the report of t-butyl gabapentin specifically but covers it in a generic way.

The tertiary butyl group has been known as an anchoring substituent on the cyclohexane ring occupying exclusively the equatorial confirmation in the ring. Therefore, if one were to synthesize 1-aminomethyl cyclohexane-1-acetic acids with a 4-t-butyl group in cis or trans stereochemistry with respect to the aminomethyl group to obtain Z and E stereoisomer respectively it should be feasible to study better, the optimal conformation for good binding of 4-t-butyl gabapentin with the alpha 2 delta sub unit of the calcium channel.

However, prior art search revealed the report of 4-t-butyl gabapentin in documents U.S. Pat. No. 6,103,932 and WO 02100347 A2. U.S. Pat. No. 6,103,932 recites and claims 4-t-butyl gabapentin, and a pharmaceutically acceptable salts thereof or a prodrug thereof, while WO 2002100347A notes the use of t-butylgabapentin in the form of a prodrug without any example. The document also describes general synthetic methods for the preparation of alkyl gabapentin analogues having one or more alkyl substituents in the cyclohexane ring. There is no specific example describing the preparation of the compound 4-t-butylgabapentin. This patent also records the radio ligand-binding assay with the alpha 2 detla sub unit derived from porcine brain tissue giving an IC50 value of 200 micro M for 4-t-butyl gabapentin, again without stereochemistry, thus missing out a solution to the crucial and challenging issue of conformational identity in the native and bound states.

U.S. Pat. No. 6,103,932 describe various synthetic routes for the preparation gabapentin analogues where as WO 99114184 restricts itself to the use of a nitro methyl intermediate to obtain gabapentin analogues. In the former patent, two routes are employed: (a) an alkyl-substituted cyclohexanone is converted to a cyanocyclohexylidene acetic ester, which is treated with aqueous alcoholic sodium cyanide to 1-cyanocyclohexane acetic ester, which upon reduction gives an azaspirodecanone. Hydrolysis of the lactam with 1:1 HCl affords the alkyl substituted gabapentin hydrochloride. In the second route, an alkyl substituted cyclohexanone is treated with ethyl cyanoacetate and ammonia gas in methanol to afford a dicyano spiroglutarimide which is hydrolysed by hot concentrated sulphuric acid to an alkyl substituted cyclohexane-1,1-diacetic acid. The diacid is converted to the anhydride, which is opened up with methanol to give the half-ester acid. This is treated with ethyl chloroformate followed by sodium azide. Thermolysis of the acylazide gives an isocyanate which upon hydrolysis with concentrated hydrochloric acid yields the alkyl substituted gabapentin hydrochloride.

In WO 99114184, the method adopted is to add nitromethane to an alkyl substituted cyclohexylidene acetic ester, which upon catalytic reduction affords the alkyl-substituted azaspirodecanone. Hydrolysis with 6 N HCl and evaporation affords the alkyl substituted gabapentin hydrochloride.

U.S. Pat. No. 6,103,932 and PCT Int'l Application publication WO 99/14184 describe examples wherein the final products, gabapentin analogues are obtained only as hydrochloride salts. Thus, in order to establish the optimal conformation for the compound 4-t-butyl gabapentin, which can bind with the alpha2delta submit of the calcium channel, it is necessary to obtain cis and trans form of 4-t-butylgabapentin with high purity.

There are prior art references on gabapentin analogues with one or more methyl groups in the cyclohexane ring and publications on their binding activity. The ascertainment of the precise conformation in which the amino group in gabapentin binds to the alpha2delta subunit can have great significance in the design of newer analogues of gabapentin and more specifically alkyl gabapentin analogues. None of the prior art document reports cis and trans stereoisomers of 4-t-butylgabapentin and their process of preparation.

OBJECTS OF THE INVENTION

Main object of the invention is to report pure forms Z(cis) and E(trans) stereo isomers of 4-t-butylgabapentin.

Another object of the present invention is to synthesize EZ mixture of 4-t-butylgabapentin, separate the mixture into pure stereoisomers and characterize them by using physical methods, namely, IR, high field proton NMR and single crystal X-ray crystallography.

Yet another object of the invention is to provide Z and E stereoisomers of 4-t-butylgabapentin and its pharmaceutically acceptable salts as an agent for the treatment of neurodegenerative disorders.

BRIEF DESCRIPTION OF THE DRAWINGS

Scheme 1 depicts schematic expression of the preparation of cis and trans isomers of 4-t-butylgabapentin.

Table 1 shows the melting points, $^1$H NMR spectral data in $CD_3OD$, Mass, HPLC, and IR spectral data of E-(11) and Z-(12) isomers of 4-t-butylgabapentin. Also, it provides melting points and $^1$H NMR spectral data in $CD_3OD$ of the hydrochloride salts of 4-t-butylgabapentin isomers.

Table 2 shows the crystallographic parameters of E-(11) and Z-(12) isomers of 4-t-butylgabapentin.

FIGS. 1, 1*a*, 2 & 2*a* show the IR spectral data as follows: E-isomer (trans): 2964, 2859, 2094, 1650, 1526, 1494, 1403, 1386, 1297, 1168, 1085, 1022, 980, 944, 915, 896, 875, 790, 762, 725, 611, 592; Z-isomer (cis): 2965, 2935, 2862, 2614, 2210, 1644, 1589, 1504, 1418, 1394, 1364, 1333, 1309, 1250, 1172, 1134, 1109, 1039, 984, 880, 854, 761, 709, 629, 578.

FIGS. 3, 3a, 4 & 4a show $^{1}$H-NMR spectral data with characteristic chemical shifts of the singlets due to COCH$_2$ and N—CH$_2$ protons bing different: 2.59 and 2.87 ppm for E-isomer (11) and 2.34 and 3.01 ppm for Z-isomer (12) respectively.

Figure 1:
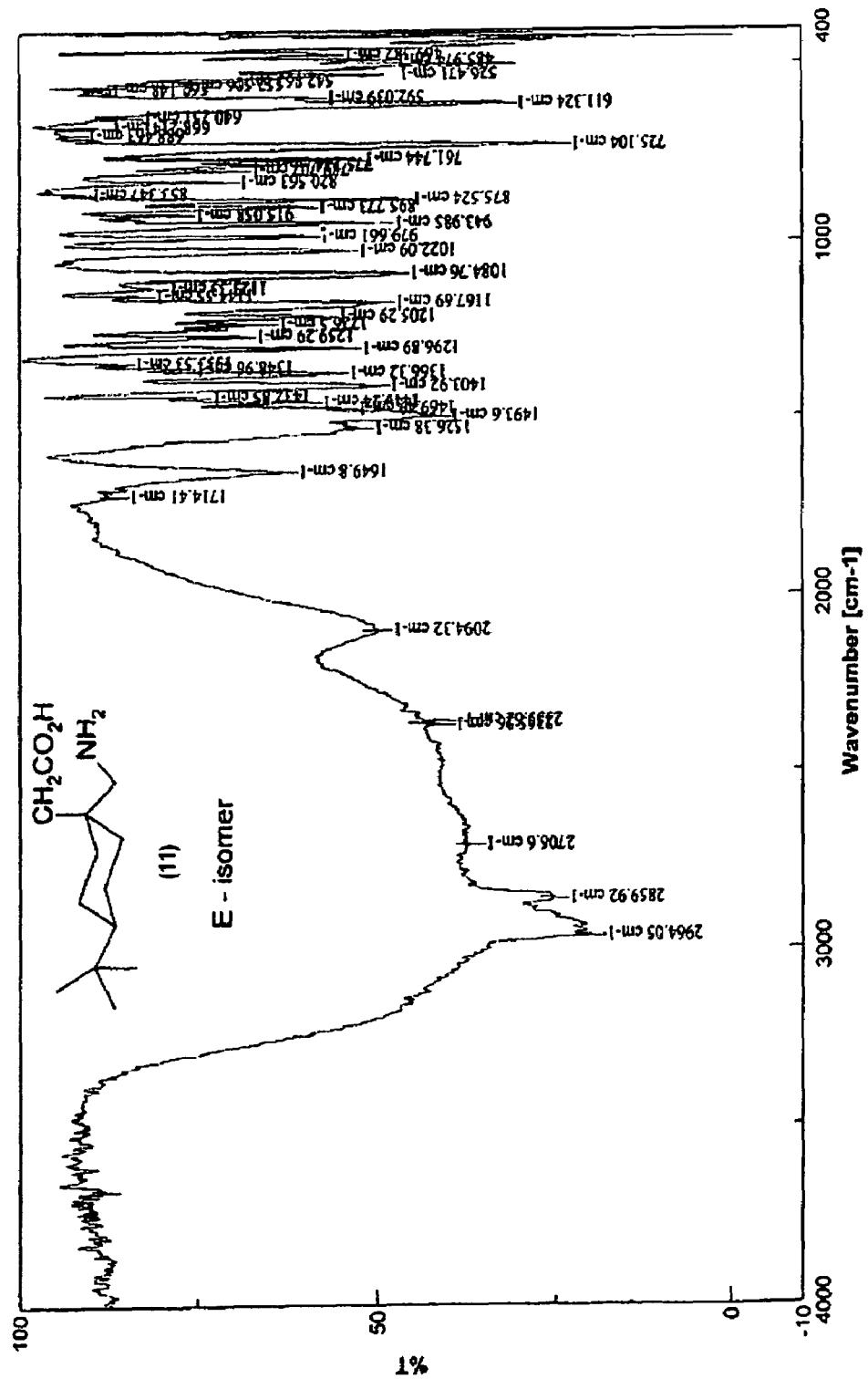
Figure 1A:
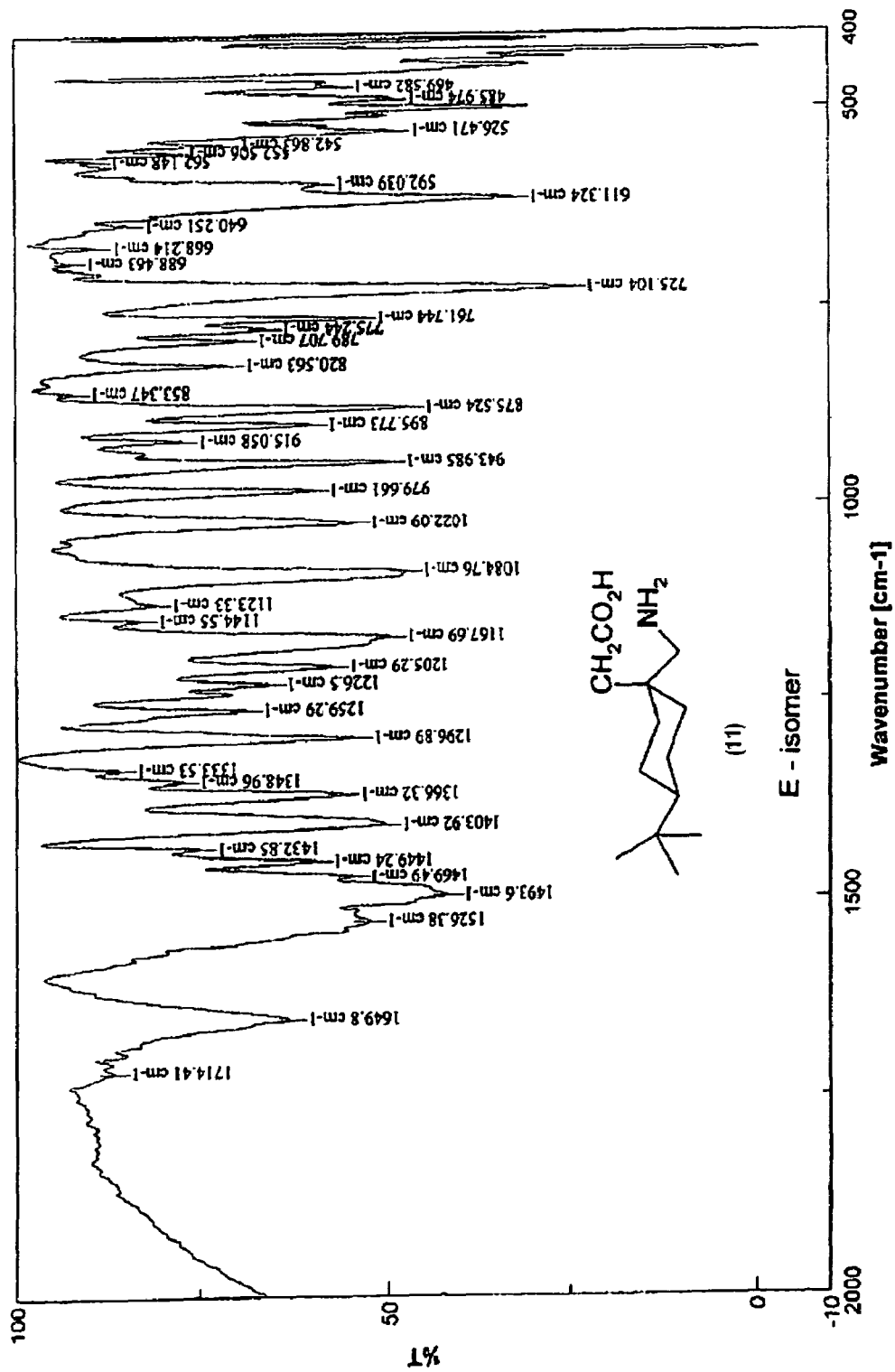
Figure 2:
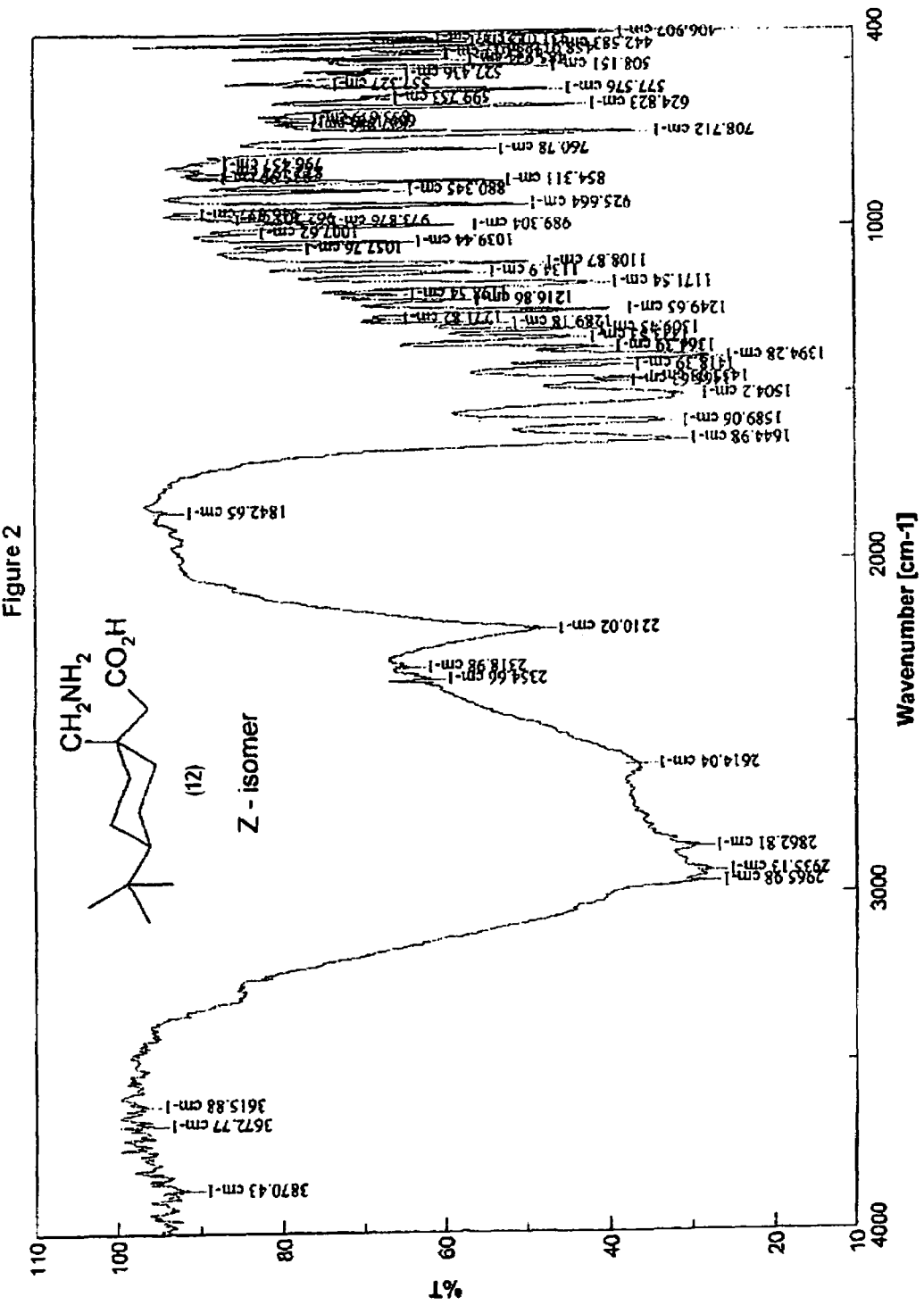
Figure 2A:
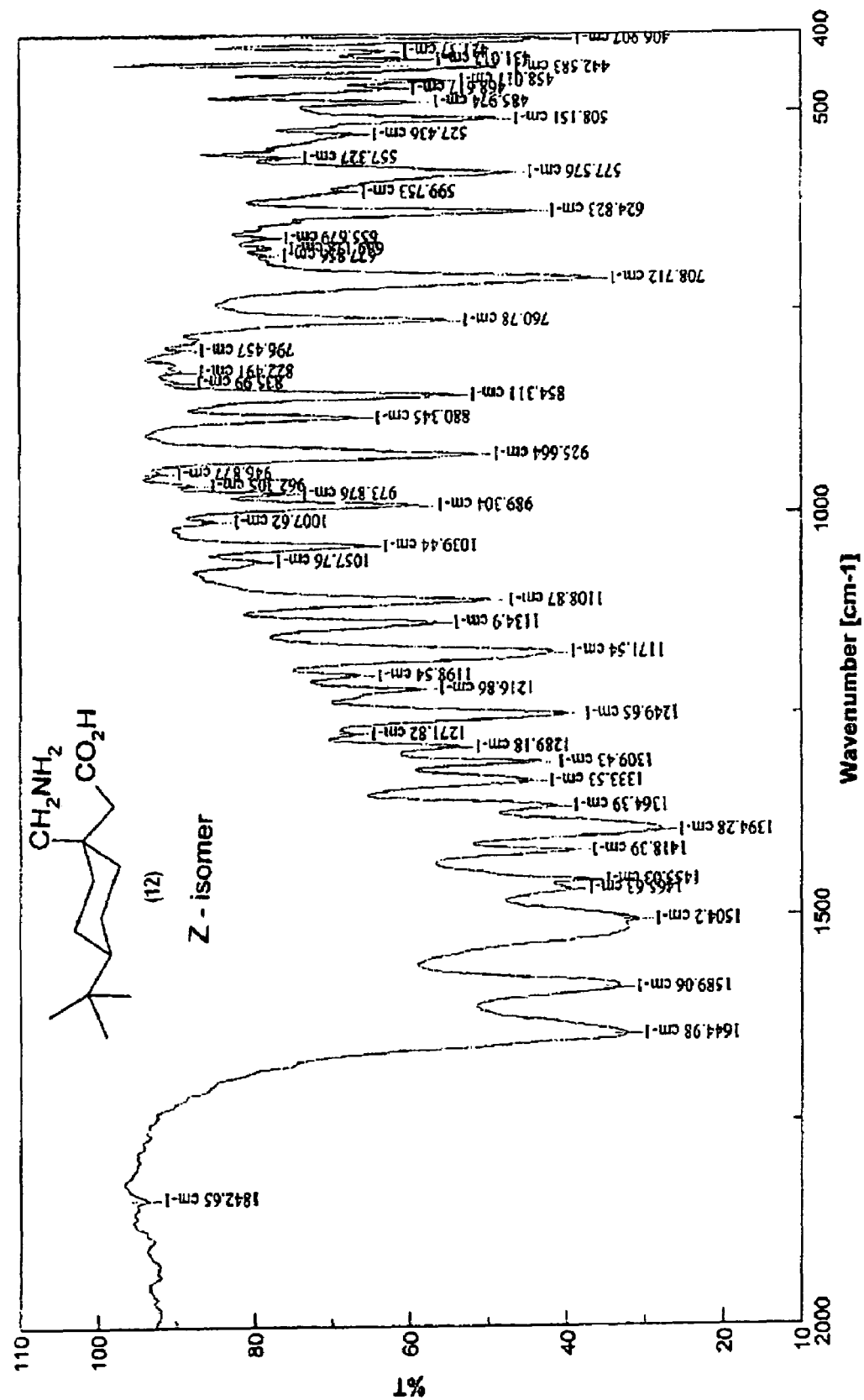
Figure 3:
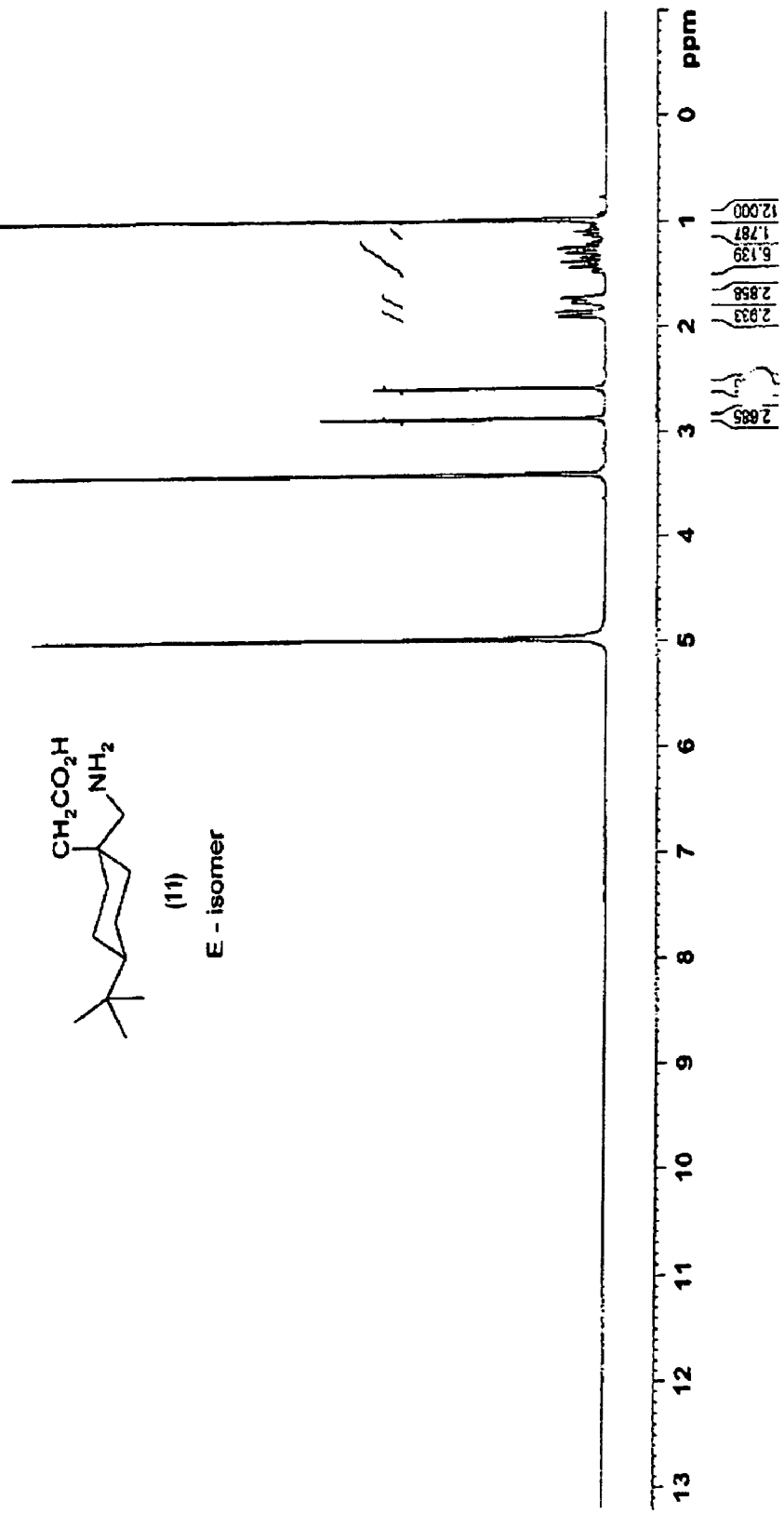
Figure 4A:
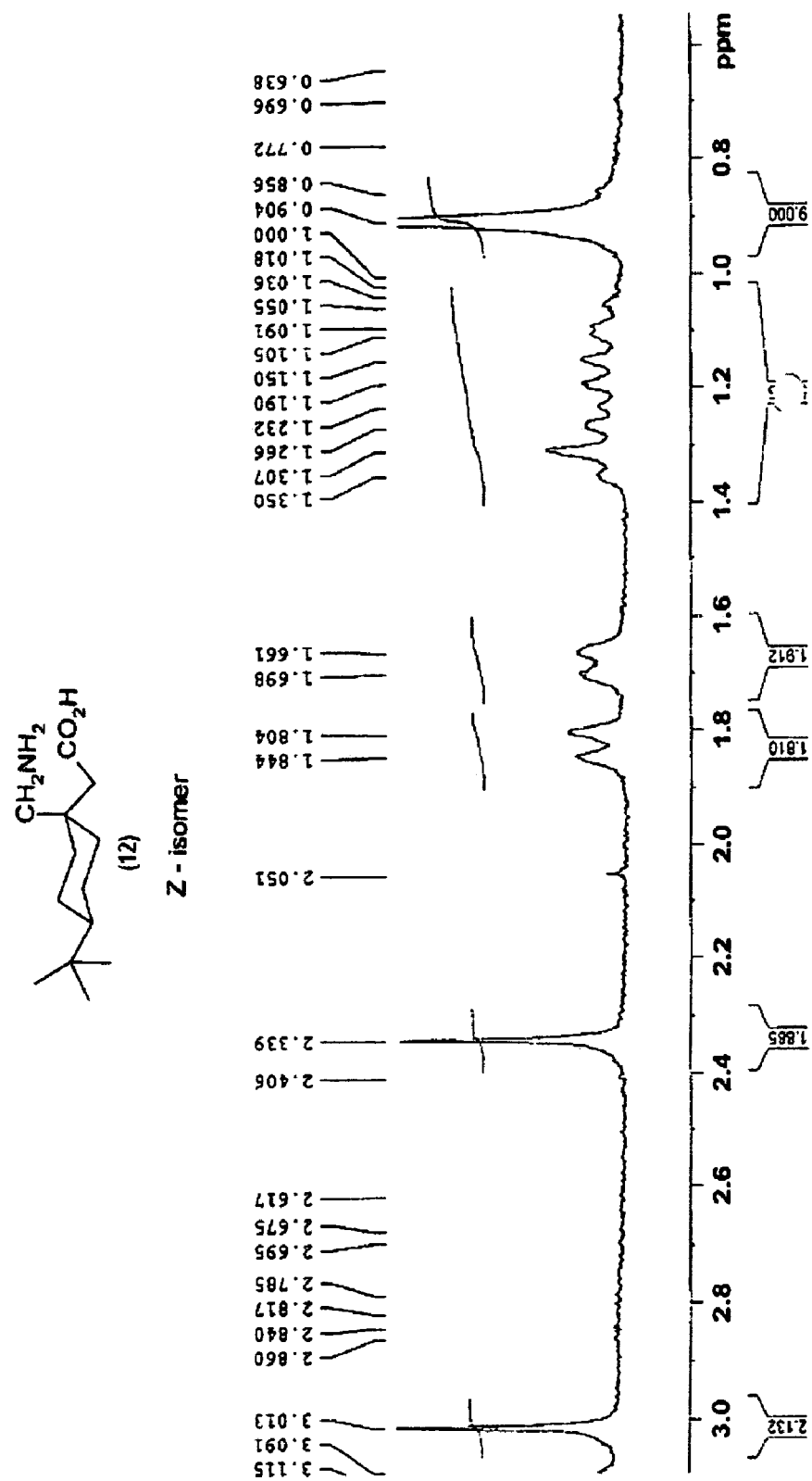
Figure 5:
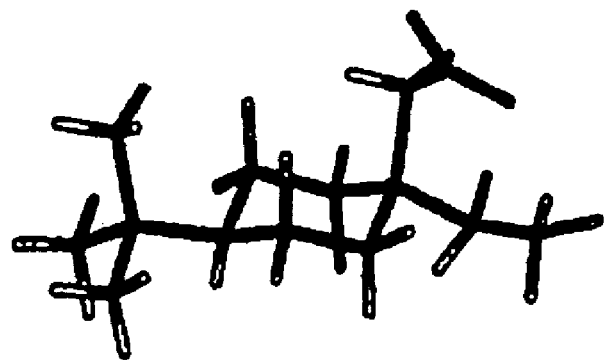
Figure 5:
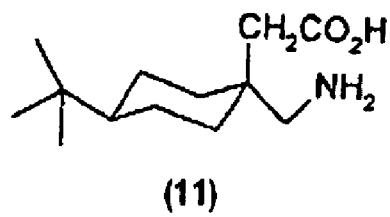
Figure 5:
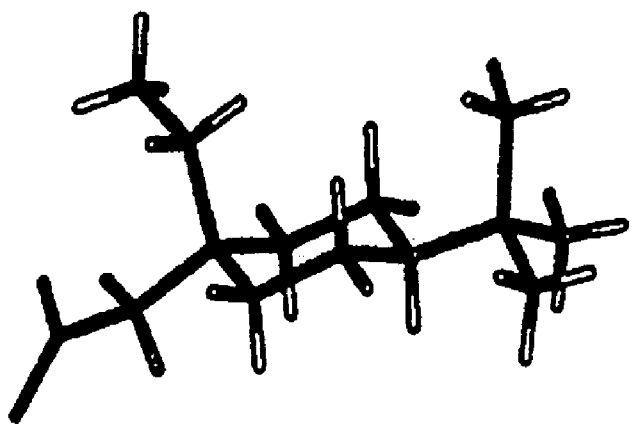
Figure 5:
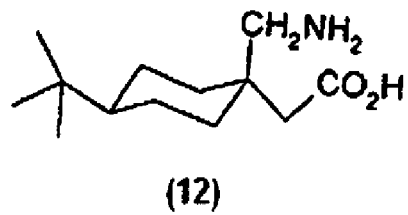

FIG. 5 shows the ORTEP (Oak Ridge Thermal Ellipsoid Plot) diagrams of E-(11) and Z-(12) isomers of 4-t-butylgabapentin, which support the structures of the isomers and orientation of the substituents in the isomers.

DESCRIPTION OF THE INVENTION

In accordance with the objects, the present invention provides a report of cis(Z) and trans(E) stereoisomers of 4-t-butylgabapentin and process for their preparation in high purity.

The single crystal structure determination by X-ray diffraction provides clinching evidence for the structures, the E-isomer (11) as expected has the t-butyl and —CH$_2$—NH$_2$ groups in trans orientation while the Z-isomer (12) has them in cis orientation.

The E-isomer (11) of 4-t-butylgabapentin has needle shaped crystals having the dimensions of 0.40×0.248×0.126 mm and the Z-isomer (12) of 4-t-butylgabapentin has thin diamond shaped crystals having the dimensions of 0.47×0.32×0.07 mm. Also, the full refinement details such as crystal system, space group, unit cell dimensions, number of formula units in unit cell (Z), linear absorption co-efficient (μ), etc., provided in Table 2 are different for the two isomers and support that the isomers are different structurally. The melting points of the E-(11) and Z-(12) isomers of 4-t-butylgabapentin base and IR and $^{1}$H-NMR spectral data show that they are pure compounds.

The process for the preparation of the cis and trans isomer of 4-t-butylgabapentin has been achieved, as outlined in Fig. I. 4-t-Butyl-cyclohexanone (I) was treated with ethylcyano acetate and ammonia in methanol to yield ammonium salt of dicyanoimide (2). Hydrolysis of (2) with hot sulfuric acid afforded the diacid (3) which was converted to the anhydride (4). (4) treated with aqueous ammonia to give the monoamide (5) as a mixture containing approximately equal proportions of stereoisomers. Reaction of (5) with sodium hypobromite solution led to the formation of lactam (6) as a mixture of stereoisomers [proton NMR (7) and its isomer with NCH$_2$ axial in the ratio of 3:2] from which one of the isomer could be crystallized out in pure form from methanol-hexane, mp 176-7° C. and its structure identified as (7) by NMR and single crystal X-ray analysis (Hydrolysis of lactam (6) with hot concentrated HCl gave a mixture of isomers of 4-t-butyl gabapentin hydrochloride (8). Crystallization of (8) from water afforded in pure form, mp 146-147° C., the isomer hemihydrate (9) with aminomethyl group in the anxial position. Dissolution of (8) in water followed by neutralization with aqueous NaOH to pH 7 precipitated the free-amino acid, surprisingly in good yield, a mixture of stereoisomers of 4-t-butyl gabapentin (10). Obviously the much poorer water solubility of (10) compared to the other gabapentin analogues is due to the presence of the more lipophilic t-butyl group. Fractional crystallization of (10) from methanol water allowed the separation of pure crystals of the E-stereoisomer (11) (trans amino methyl) mp 182-183° C. and Z-stereoisomer (12) (cis amino methyl) mp 183-184° C. of 4-t-butyl gabapentin to which structural assignments were made by high field proton NMR and X-ray diffraction.

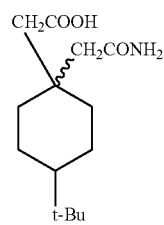

The stereoisomers and pharmaceutically acceptable salts of the present invention can be used as an agent for the treatment of neurodegenerative disorders. A pharmaceutical composition comprising an effective amount of these compounds may be used for the treatment.

The present invention is illustrated with following example and should not be construed to limit the scope of the invention.

EXAMPLE

Preparation of Z(cis) and E(trans) stereoisomers of 4-t-butyl gabapentin

Step-1 Preparation of ammonium salt of 1,5-dicyano-2,4-dioxo-9-t-butyl-3-azaspiroundecane (2)

204 gms (1.32 mole) of 4-t-butyl cyclohexanone and 299.3 gms (2.64 mole) of ethyl cyano acetate were mixed, cooled to −5° C. and treated with 640 ml of 15% wt/vol methanolic ammonia (pre-cooled to −5° C.) at −5° to 0° C., slowly over a period 90 minutes. The combined mixture was stirred for 1 hour and refrigerated at −5° to 0° C. for a time period 96 hr. A thick product was formed and was filtered and washed with 100 ml of chilled methanol and dried to get the ammonium salt of 1,5-dicyano-2,4-dioxo-9-t-butyl-3-azaspiroundecane (2); mp 238-240° C.

Step-2 Preparation of 4-t-butylcyclohexyl-1,1-diacetic acid (3)

300 ml of 60% sulphuric acid (wt/vol) was heated to 125-130° C. 89 gms of the ammonium salt (2) of step (1) was added in small portions to the hot sulphuric acid mixture at about 125-130° C. During the addition of the salt, the reaction was exothermic and at the end of the addition which was completed over a period of 3 hrs, the temperature was allowed to rise up to 140° C. The reaction mixture was maintained at 130-140° C. for 15 hrs. Then it was cooled to 25-30° C. and the ash coloured solid was filtered. This crude diacid was washed with 200 ml of water.

Then the wet product was suspended in 300 ml of 20% ammonia solution, warmed and filtered over a bed of hyflo supercel. The clear filtrate was acidified with concentrated HCl to get pure 4-t-butylcyclohexyl-1,1-diaceticacid (3), which was dried at 60-70° C.; mp 178-183° C.

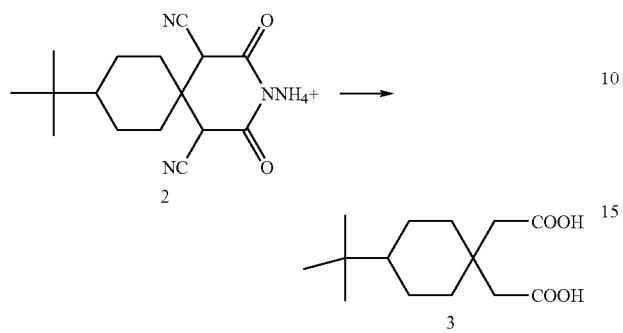

Step-3 Preparation of 4-t-butylcyclohexyl-1,1-diaceticacid monoamide (5)

28.8 gms of 4-t-butyl cyclohexyl-1,1-diacetic acid (3) was refluxed with 47.7 gms (0.6 mole) of freshly distilled acetyl chloride for 3 hrs. The volatiles were distilled at around 80° C. in water bath under vacuum to obtain as anhydride (4) which was quenched in 100 ml of aqueous ammonia. The resultant aqueous ammonia was stirred for 30 minutes at 25-30° C. and washed with toluene to remove neutral impurities. The purified ammonium salt solution was acidified to pH 1-2 with concentrated HCl. The solid precipitated was filtered and dried at 60-70° C. to get 4-t-butyl cyclohexyl-1,1-diacetic acid mono amide (5), mp: 176-180° C.

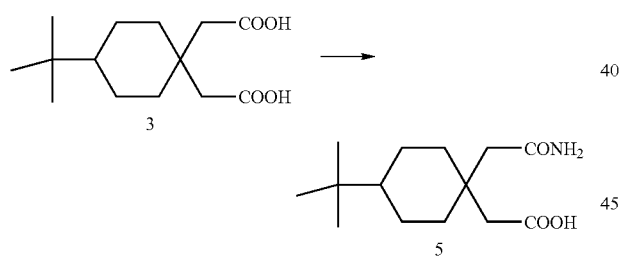

Step-4 Preparation of 8-t-butyl-azaspiro [4,5]-undecan-3-one (6)

15.68 gms (0.39 mole) of sodium hydroxide was dissolved in 110.5 ml of water and chilled to 0-5° C. To this 12.86 gms (0.08 mole) of bromine was added over 30 min. followed by 20 gms of (5) which was added in several lots at 0 to −5° C. The reaction mixture was stirred at the same temperature for 30 min. It was then heated slowly over an hour to 80-85° C., and the temperature maintained at 80-85° C. for 6 hr. The reaction mixture was now cooled to 25-30° C. and extracted with 300 ml of ethylene dichloride (EDC). The aqueous layer was again heated to 80-85° C., cooled and extracted with 300 ml of EDC. Both EDC layers were combined and distilled to obtain a mixture of stereoisomeres of t-butylgabalactam (6), m.p 150-154° C., which was almost white in colour. Crystallization of (6) from methanol-hexane gave one of the isomer (7) in pure form mp 176-177° C.

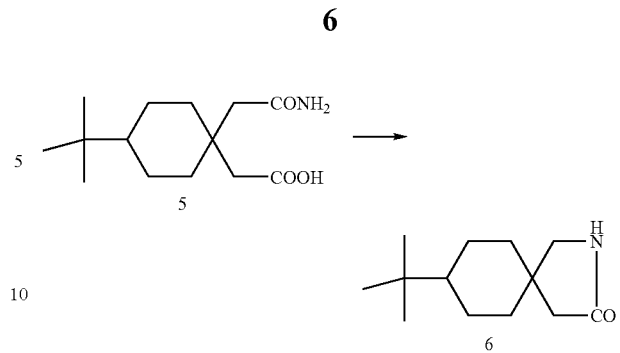

Step-5 Preparation of t-butylgabapentin hydrochloride (8)

2 gms of t-butylgabalactam (6) (0.009 mole) was heated with 5 ml of concentrated HCl at 95-100° C. for 16 hrs. The resultant clear solution was cooled to 70° C. when a solid separated; 5 ml toluene was added, the mixture further cooled to 30° C. and filtered to get t-butyl gabapentin hydrochloride. The aqueous portion of the mother liquor was separated and heated to 95-100° C. for 8 hr. The clear solution was cooled and 5 ml toluene was added. The solid formed again was filtered to get another crop of the t-butylgabapentin hydrochloride. Both the crops were combined and stirred with 10 ml of acetone for 30 min. The product was filtered to get 4-t-butylgabapentin hydrochloride (8) as a mixture of cis and trans isomers, m.p 172-180° C. Crystallization from water gave one of the isomer (9) in the pure form as a hemihydrate; mp 146-147° C.

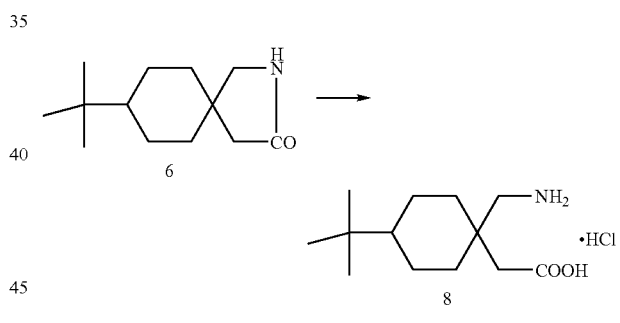

Step-6 Preparation of 4-t-butylgabapentin (10)

2 gms of (0.0076 mole) of 4-t-butylgabapentin hydrochloride (8) was dissolved in 4 ml water. The clear solution was heated to 45-50° C., treated with charcoal and filtered. The filtrate was neutralized with 10% sodium hydroxide solution to pH 7. The solid precipitate was filtered and was washed with 2ml water. The wet product was warmed with 10 ml of methanol, filtered at room temperature and dried to afford the mixture of cis and trans 4-t-butyl-gabapentin (10); mp 176-180° C.

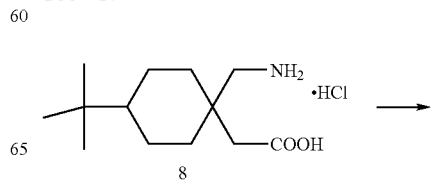

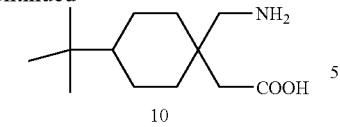

Step-7 Preparation of E and Z isomers of 4-t-butyl gabapentin

Compound (10) on crystallization from MeOH/EtOH/H$_2$O yielded two forms of conformational isomers E and Z designated as (11) and (12) respectively.

E (11), mp 182-183° C.

Z (12), mp 183-184° C.

The structures of (11) and (12) were determined by NMR and X-ray diffraction data.

What is claimed is:

1. A purified and isolated (E) isomer of 4-tert-butylgabapentin of formula (11)

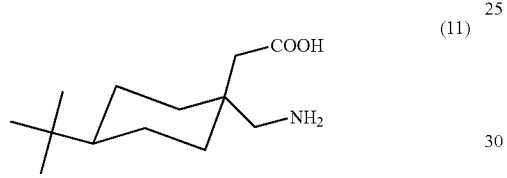

characterized by bands in the IR spectrum at 2964, 2859, 2094, 1650, 1526, 1494, 1403, 1386, 1297, 1168, 1085, 1022, 980, 944, 915, 896, 875, 790, 762, 725, 611 and 592±2 cm$^{-1}$.

2. A purified and isolated (Z) isomer of 4-tert-butylgabapentin of formula (12)

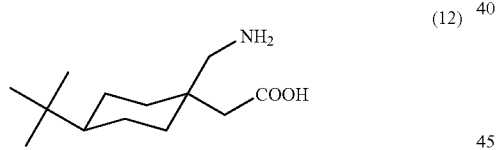

characterized by bands in the IR spectrum at 2965, 2935, 2862, 2614, 2210, 1644, 1589, 1504, 1418, 1394, 1364, 1333, 1309, 1250, 1172, 1134, 1109, 1039, 984, 880, 854, 761, 709, 629, and 578±2 cm$^{-1}$.

3. A process for the preparation of a purified and isolated E isomer (11) of 4-tert-butylgabapentin of formula (11)

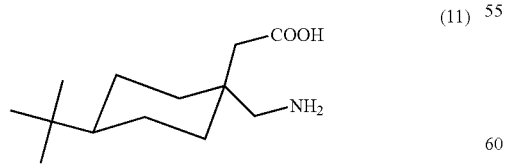

characterized by bands in the IR spectrum at 2964, 2859, 2094, 1650, 1526, 1494, 1403, 1386, 1297, 1168, 1085, 1022, 980, 944, 915, 896, 875, 790, 762, 725, 611 and 592±2 cm$^{-1}$ or a purified and isolated Z isomer (12) of 4-tert-butylgabapentin of formula (12)

characterized by bands in the IR spectrum at 2965, 2935, 2862, 2614, 2210, 1644, 1589, 1504, 1418, 1394, 1364, 1333, 1309, 1250, 1172, 1134, 1109, 1039, 984, 880, 854, 761, 709, 629, and 578±2 cm$^{-1}$, the process comprising:

(a) contacting 4-t-butyl cyclohexanone (1) with cyanoacetate and ammonia in a solvent at a temperature ranging between -5 to 0° C. for a period of up to 96 h to obtain ammonium salt of dicyanoimide (2),

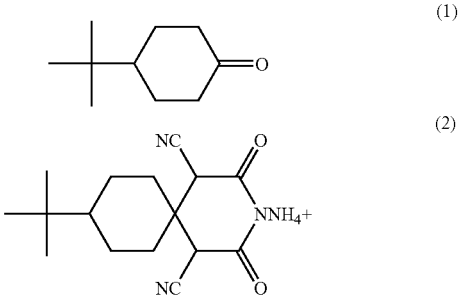

(b) hydrolyzing ammonium salt of dicyanoimide (2) of step (a) with hot sulfuric acid at a temperature ranging between 125° to 140° for a period of 3 h to yield diacid (3),

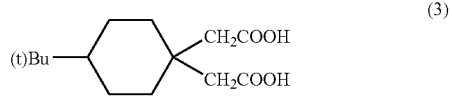

(c) converting diacid (3) of step (b) to its anhydride (4), quenching (4) in aqueous ammonia to obtain monoamide (5) and washing with an aromatic hydrocarbon solvent,

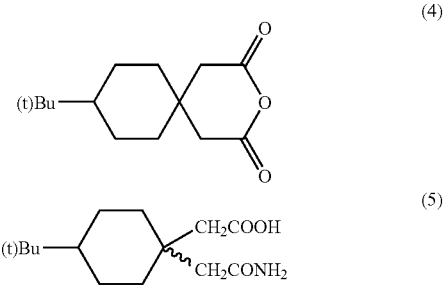

(d) treating monoamide (5) with aqueous sodium hypobromite solution by gradually raising the temperature from −5° C. to 85° C. over a period of an hour, maintaining the temperature for about further 6 h, cooling to 25° to 30° C., extracting with haloalkane solvent, to obtain (cis, trans) mixture of lactam (6),

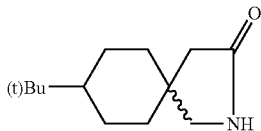

(e) hydrolyzing lactam (6) with concentrated hydrochloric acid at a temperature ranging between 95° and 100° C. to obtain (cis, trans) mixture of 4-t-butlygabapentin hydrochloride (8),

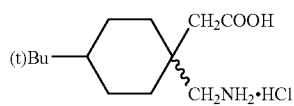

(f) neutralizing aqueous solution of compound (8) after treating with charcoal followed by alkali to pH 7.0 to obtain (cis, trans) mixture of 4-t-butylgabapentin (10), and

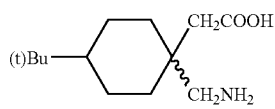

(g) crystallizing compound (10) from a mixture of methanol-ethanol-water to obtain pure form of stereoisomers trans (E) and cis (Z) of 4-t-butylgabapentin (11) and (12).

4. An intermediate compound of formula (5)

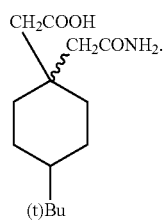

5. The process of claim 3, wherein the solvent of (a) is methanol.

6. The process of claim 3, wherein the aromatic hydrocarbon solvent of (c) is toluene.

7. The process of claim 3, wherein the haloalkane solvent of (d) is ethylenedichloride.

8. A method of treating neurodegenerative diseases comprising administering to a patient in need thereof a therapeutically effective amount of the compound of claim 1.

9. A method of treating neurodegenerative diseases comprising administering to a patient in need thereof a therapeutically effective amount of the compound of claim 2.

10. A method of inhibiting alpha-2-delta calcium channel comprising administering a compound of claim 1.

11. A method of inhibiting alpha-2-delta calcium channel comprising administering a compound of claim 2.

12. The (E) isomer of claim 1 further characterized by peaks in a powder X-ray diffraction pattern at 4.20, 6.52, 7.34, 7.56, 7.68, 8.30, 8.40, 8.74, 9.30, 9.62, 9.92, 10.34, 11.18, 11.38, 12.36, 13.06, 14.06, 14.42, 14.96, 15.50, 16.62 and 18.62 ±1 degrees two-theta.

13. The (Z) isomer of claim 2 further characterized by peaks in a powder X-ray diffraction pattern at 4.14, 7.08, 7.36, 7.86, 8.00, 8.30, 9.04, 10.02, 10.20, 10.40, 10.72, 12.46, 14.28, 15.28, 15.76, 16.74 and 19.06±1 degrees two-theta.

14. The process of claim 3, wherein the purified and isolated compound is the E isomer (11) of 4-tert-butylgabapentin of formula (11)

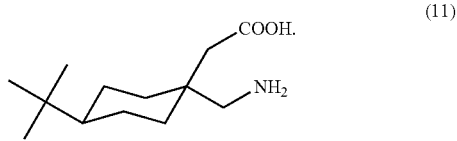

15. The process of claim 3, wherein the purified and isolated compound is the Z isomer (12) of 4-tert-butylgabapentin of formula (12)

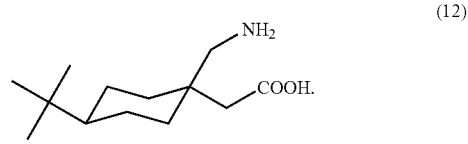

* * * * *

UNITED STATES PATENT AND TRADEMARK OFFICE
CERTIFICATE OF CORRECTION

PATENT NO. : 7,632,864 B2  Page 1 of 1
APPLICATION NO. : 11/583953
DATED : December 15, 2009
INVENTOR(S) : Nagarajan Kuppuswamy et al.

It is certified that error appears in the above-identified patent and that said Letters Patent is hereby corrected as shown below:

Column 8, Line 34, change "to 140°" to --to 140° C.--.

Column 9, Line 12, change "4-t-butlygabapentin" to --4-t-butylgabapentin--.

Signed and Sealed this

Thirtieth Day of March, 2010

David J. Kappos
*Director of the United States Patent and Trademark Office*